United States Patent [19]
Goodrich, Jr. et al.

[11] Patent Number: 5,213,814
[45] Date of Patent: May 25, 1993

[54] LYOPHILIZED AND RECONSTITUTED BLOOD PLATELET COMPOSITIONS

[75] Inventors: Raymond P. Goodrich, Jr.; Victoria A. Wong, both of Pasadena, Calif.

[73] Assignee: Cryopharm Corporation, Pasadena, Calif.

[21] Appl. No.: 525,392

[22] Filed: May 17, 1990

Related U.S. Application Data

[63] Continuation-in-part of Ser. No. 378,349, Jul. 11, 1989, Pat. No. 5,045,446, and Ser. No. 360,386, Jun. 2, 1989, Pat. No. 5,043,261, which is a continuation of Ser. No. 335,557, Apr. 10, 1989, abandoned, which is a continuation-in-part of Ser. No. 195,745, May 18, 1988, abandoned, and Ser. No. 237,583, Aug. 25, 1988, abandoned.

[51] Int. Cl.$^5$ ............................................... A61K 35/14
[52] U.S. Cl. ......................................... 424/532; 435/2
[58] Field of Search ............................. 424/532; 435/2

[56] References Cited

U.S. PATENT DOCUMENTS

| | | | |
|---|---|---|---|
| 2,786,014 | 3/1957 | Tullis | 424/532 |
| 4,059,967 | 11/1977 | Rowe et al. | 424/532 |
| 4,764,463 | 8/1988 | Mason et al. | 424/532 |
| 4,874,690 | 10/1989 | Goodrich et al. | 435/2 |
| 4,973,327 | 11/1990 | Goodrich et al. | 604/408 |
| 5,153,004 | 10/1992 | Goodrich et al. | 435/2 |

*Primary Examiner*—Sam Rosen
*Attorney, Agent, or Firm*—Heller, Ehrman, White & McAuliffe

[57] ABSTRACT

A process and medium are disclosed for the lyophilization of cells, specifically platelets, and cell-like matter, which comprises the use of solutions including monosaccharide hexoses and pentoses, and biocompatible amphipathic polymers to permit the reconstitution of transfusably useful cells, specifically platelets, and cell-like matter.

36 Claims, No Drawings

LYOPHILIZED AND RECONSTITUTED BLOOD PLATELET COMPOSITIONS

This application is a continuation-in-part of copending commonly assigned Ser. No. 378,349 filed Jul. 11, 1989 now U.S. Pat. No. 5,045,446, and of Ser. No. 360,386, filed Jun. 2, 1989, now U.S. Pat. No. 5,043,261 the latter of which is a continuation of copending commonly assigned Ser. No. 335,557 filed Apr. 10, 1989 now abandoned; which is a continuation-in-part of Ser. Nos. 195,745 filed May 18, 1988, now abandoned and 237,583, filed Aug. 25, 1988, now abandoned, the disclosures of which are incorporated herein by reference in their entirety.

FIELD OF THE INVENTION

This invention relates to the general field of biochemistry and medical sciences, and specifically to novel lyophilized and reconstituted cell, and specifically, platelet compositions.

BACKGROUND OF THE INVENTION

Blood is a major tissue of the human body, and has a predominant role the delivery of oxygen from the lungs to peripheral tissues. This role is carried out by erythrocytes, i.e., red blood cells (RBC). The oxygen is furnished to the peripheral cells from the lungs by an exchange-diffusion system brought about by a red, iron-containing protein called hemoglobin. When hemoglobin combines with oxygen, oxyhemoglobin is formed and when oxygen is given up to the tissues, the oxyhemoglobin is reduced to deoxyhemoglobin.

The red cell membrane is composed of two major structural units, the membrane bilayer and a cytoskeleton. A lipid bilayer and integral membrane proteins form the membrane bilayer, which has little structural strength and fragments readily by vesiculation. The other major component, the membrane skeleton, stabilizes the membrane bilayer and provides resistance to deformation. The cytoskeleton is linked to the bilayer in the erythrocyte membrane, possibly by lipid-protein as well as protein-protein associations. The hemoglobin, and other RBC components, are contained within the red cell membrane.

In adults, bone marrow is active in the formation of new red blood cells. Once erythrocytes enter the blood, these cells have an average lifetime of about 120 days. In an average person, about 0.83% of the erythrocytes are destroyed each day by phagocytosis, hemolysis or mechanical damage in the body, and the depleted cells are renewed from the bone marrow.

A wide variety of injuries and medical procedures require the transfusion of whole blood or a variety of blood components. Every patient does not require whole blood and, in fact, the presence of all of the blood components can cause medical problems. Separate blood fractions, such as erythrocytes and platelets, can be stored under those special conditions best suited to assure their biological activity at the time of transfusion. For example, when donor blood is received at a processing center erythrocytes are separated and stored by various methods. Such cells are storable in citrate-phosphate-dextrose at 4° C. for up to five weeks, generally as a unit of packed erythrocytes having a volume of from 200 to 300 ml and a hematocrit value (expressed as corpuscular volume percent) of 70 to 90. Erythrocytes may also be treated with glycerol and then frozen at from $-30°$ to $-196°$ C. and stored for up to seven years in a glycerol solution, but must be kept frozen at low temperatures in order to survive sufficiently for transfusion. Both these methods require careful maintenance of storage temperature to avoid disruption of the desired biological activity of the erythrocytes, and provide a twenty-four hour survival time for at least 70% of the transfused cells, which is considered to be an acceptable level for use in transfusion practice in accordance with the American Association of Blood Bank standards.

It has thus been a desideratum to obtain reconstitutable cells, particularly red blood cells and platelets, which can be stored at high storage temperatures (4° C. to room temperatures) with good shelf life.

Prior to the present invention, it has been believed to be impossible to freeze-dry cells in a manner which permits the reconstitution with an intact cytoskeleton and, in the case of erythrocytes, with biologically-active hemoglobin, i.e., viable red blood cells. Viable RBC's can be characterized by one or more of the following: capability of synthesizing ATP; cell morphology; $P_{50}$ values; oxy, met and heme values; MCV, MCH, and MCHC values; cell enzyme activity; and in vivo survival. When RBC's have been lyophilized according to previous methods, for example in either an aqueous or phosphate-buffered saline (PBS) solution, the reconstituted cells are damaged to the extent that the cells are not capable of metabolizing or synthesizing ATP, and the cell hemoglobin cannot transport oxygen. Glutaraldehyde-fixed erythrocytes, which have been lyophilized and reconstituted, have found use primarily in agglutination assays.

Platelets are single cells in the circulation involved in the process of hemostasis. They are involved directly in the coagulation process. In cases where damage to vascular tissue occurs, platelets act by adherence to collagen and basement membranes which have been exposed. Following adherence, there is a release of constituents from intracellular granules. These compounds promote vasoconstriction, and aggregation of other platelets in the area of damage. The consequences of this behavior are an arresting of bleeding in damaged blood vessels and stimulation of coagulation.

Platelets consist of fragments of megakaryocyte mother cells. They range from 5 $\mu m^3$ to 12 $\mu m^3$ in size with an average of 7.1–7.5 $\mu m^3$. They are shaped like discs with numerous invaginations in the membrane. It is covered by a protein coat which is involved in the activation of coagulation. The membrane is composed of phospholipids, beneath which are submembranous filaments of actomyosin.

Platelets are formed from megakaryocytes in the bone marrow. They enter the circulation by fragmentation of the megakaryocyte. They survive in the circulation for about 10 days. Most remain in the general circulation, but about one third remain as a pool in the spleen.

A variety of injuries calls for the transfusion of platelets. Most involve cases in which bleeding is excessive. Platelets are generally storable after separation from whole blood which had been drawn into citrate-dextrose-phosphate-adenine (CPDA). This separation must normally be performed within six hours of collection with the blood at room temperature (22°). The platelets are normally stored as concentrates in containers composed of polyolefin for periods up to 5–7 days at room temperature. The risks of bacterial growth in solutions stored at room temperature for this period limits the time during which platelets may be used in transfusion medicine to five days, as established by the FDA. Storage in liquid form at temperatures below room temperature leads to substantial loss in platelet functions such as platelet aggregation and release responses, membrane glycoprotein expression, etc. Solutions such as DMSO devised for freezing platelets pose problems due to toxicity and the ability of the platelets to withstand freezing.

It has also been a desideratum, therefore, to obtain cells, particularly platelets, which could be stored for prolonged periods of time at high storage temperatures (4° C. to RT). Prior to the present invention, it has been believed impossible to freeze-dry cells, including platelets, in a manner which permits their reconstitution with intact membranes, functional enzymes, and preserved aggregation, release, and phagocytosis responses, i.e., viable platelets. Viable platelets can be characterized by one or more of the preceding characteristics. When platelets have been lyophilized according to previous methods, for example in PBS, the reconstituted cells do not have intact membranes, do not exhibit normal morphologies, are not capable of aggregating upon stimulating with ADP, and do not exhibit normal phagocytosis.

SUMMARY OF THE INVENTION

The compositions provided by the present invention allow for storage of cells and specifically platelets under normal conditions, while maintaining, in the case of cells, the structure of the cell. The compositions of the present invention may be reconstituted and used on a therapeutic level. Briefly, the compositions are made by immersing a plurality of cells or cell-like matter (such as hemosomes), and specifically platelets in a physiologically buffered aqueous solution containing a carbohydrate, and a biologically compatible polymer, or mixture of polymers, preferably having amphipathic properties. By the term amphipathic it is meant there are hydrophobic and hydrophilic portions on a single molecule. This immersion is followed by freezing the solution, and drying the frozen solution to yield novel freeze-dried cells containing less than 10%, and preferably about 3% or less by weight of moisture, which, when reconstituted, produce a significant percentage of viable, transfusably useful cells, such as red blood cells or platelets, or cell-like material such as hemosomes. Methods of reconstitution of the cells are also provided.

DETAILED DESCRIPTION OF THE INVENTION

The carbohydrate utilized to prepare cell, specifically platelets, or cell-like material such as hemosomes, according to the invention is biologically compatible with the cells or hemosomes, that is, non-disruptive to the cells or hemosome membrane, and one which permeates, or is capable of permeating, the membrane of the cell or hemosome. The carbohydrate may be selected from the group consisting of monosaccharides, since disaccharides do not appear to permeate the membrane to any significant extent. Monosaccharide pentoses and hexoses are preferred as is a final concentration of from about 7.0 to 37.5 weight % in phosphate buffered saline (PBS), preferably about 26%. Xylose, glucose, ribose, mannose and fructose are employed to particular advantage.

The invention will be hereafter described in connection with platelets, but it will be understood it is also applicable to other types of cells, particularly to those found in blood, to cell-like material (hemosomes) and to red blood cells.

The polymer may be present in the solution in concentrations of from a final concentration of about 0.7 weight % up to saturation, and has a molecular weight in the range of from about 1K to about 600K. Preferably, the polymer has a molecular weight in the range of from about 2.5K to about 360K, most preferably from about 5K to 50K, and is present in a concentration of from about 3.6 weight % up to the limit of solubility of the polymer in the solution. Polymers selected from the group consisting of polyvinylpyrrolidone (PVP) and polyvinylpyrrolidone derivatives, and dextran and dextran derivatives provide significant advantages. Most preferred is the use of polyvinylpyrrolidone (an amphipathic polymer) of average molecular weight of in the range of 10–40K in an amount in the range of 12–20% weight to volume in the solution prior to lyophilization. Amino acid based polymers (i.e., proteins), dextrans or hydroxyethyl starch may also be employed. Other amphipathic polymers may be used, such as poloxamers in any of their various forms. The use of the carbohydrate-polymer solution in the lyophilization of platelets allows for the recovery of intact cells, a significant percentage of which has normal morphologies, is capable of aggregating upon stimulation with ADP, and exhibits normal phagocytocis. While not intending to be bound by any theory, the amphipathic properties of the polymer allow them to bind to the cell membrane while protecting the membrane surface by extension of the hydrophilic portion into the aqueous environment. This may alleviate the damage to the cell membrane which causes other problems, such as cell aggregation.

As noted above, the process of the invention provides a medium for the lyophilization and reconstitution of intact and biologically-active platelets. While the media of the invention are novel it will be understood that apparatus and related techniques are known by those of skill in the art for the lyophilization of various materials, and cells in particular, and only the specific temperatures and apparatus employed in the examples are described herein. From this description, one of ordinary skill in the art will be capable of employing the media of the invention in a process for the freeze-drying and reconstitution of intact, viable platelets.

The term lyophilization is broadly defined as freezing a substance and then reducing the concentration of one of the solutes, namely water, by sublimation and desorption, to levels which will no longer support biological or chemical reactions. Usually, the drying step is accomplished in a high vacuum. However, with respect to the storage of cells and particularly platelets, the extent of drying (the amount of residual moisture) is of critical importance in the ability of cells to withstand long-term storage at room temperature. In the method of the invention, cells may be lyophilized to a residual water content of less than 10 weight %, preferably less than 3%, and still be reconstituted to transfusable, therapeutically useful cells.

The lyophilization solution will be buffered in the range of pH of 7.0 to 7.4 preferably by a phosphate-buffered saline solution. A typical phosphate-buffered saline solution will comprise mono- and di-basic sodium phosphate (usually around 10 mM), sodium chloride (usually about 150 mM). This solution maintains the pH at around 7.2.

A preferred phosphate-buffered saline (PBS) solution to be used as the lyophilization buffer will comprise pyruvate, inosine, adenine, potassium chloride, sodium chloride, and dipotassium phosphate, all of which will serve as a basic salt buffer at a pH of about 7.2. In addition this lyophilization buffer will contain a final concentration of about 30% weight by volume of a monosaccharide, preferably 26% (1.44M) glucose, and a final concentration of about 16% weight by volume of a polymer, preferably polyvinylpyrrolidone (average molecular weight of 24K).

A mixture of polymers, preferably amphipathic polymers, may be used instead of a single polymer. The mixture of polymers may be present in the buffered lyophilization solution in total concentrations of from 0.7% (by weight) up to saturation. Preferably, each of the polymer types in the mixture has a molecular weight in the range of from about 1K to about 600K (number average molecular weight). Preferably, at least one of the types of polymers of the mixture will have a molecular weight from about 1K to 400K, and most preferably from 2.5K to 360K. Each of the polymer types may be present in a concentration of from bout 3.5% (by weight) up to its limit of solubility in the buffered lyophilization solution. Also, one of the types of polymers of the mixture will have a molecular weight in the range of about 100K to about 600K, most preferably in the range of about 100-500K. Polymers selected from the group consisting of polyvinylpyrrolidone (PVP), polyvinylpyrrolidone derivatives, dextran, dextran derivatives, amino acid based polymers (i.e., proteins) and hydroxyethyl starch (HES) may be employed. Other amphipathic polymers may be used, such as poloxamers in any of their various forms. In a preferred embodiment, a mixture of 5% PVP (molecular weight of about 24K) and 15% HES (molecular weight in the range of about 100K-500K) is employed in the buffered lyophilization solution.

The platelets will preferably be prepared from whole blood centrifugation, removal of the plasma supernatant and platelets, then the platelets are diluted with the lyophilization buffer described above so that the final diluted concentration of carbohydrate and polymer are maintained in the necessary ranges.

Alternatively, commercially available packed platelet concentrates may be used, which typically are prepared in CPDA (commercial solution containing citrate, phosphate, dextrose and adenine).

Upon lyophilization by conventional techniques to a moisture content of less than 10%, and preferably less than 3%, the lyophilized cells may be maintained under vacuum in vacuum-tight containers, or under nitrogen or other inert gas, at room temperatures for extended periods of time in absence of or without significant degradation of their desirable properties when reconstituted for use as transfusable cells. It is a particular advantage of the present invention that the lyophilized cells may be stored at room temperature for extended periods of time.

It is a further advantage of the present invention that the lyophilized platelets may be reconstituted at normal temperatures, i.e. greater than about 17° C. up to about 37° C., which corresponds to normal human body temperature, and preferably at room temperature (about 22° C.). The reconstitution medium is preferably a solution comprising a polymer or mixture of polymers having a molecular weight of from about 1K to 360K, preferably 5K to about 360K, present in a concentration in the range of about 10 to 30% weight by volume. This polymer may be the same polymer utilized to lyophilize the red blood cells as described above. Hence the polymers polyvinylpyrrolidone, hydroxyethyl starch, and dextran are particularly preferred and most preferred is polyvinylpyrrolidone present in a concentration of about 19% weight by volume in the reconstitution solution. The reconstitution solution will be buffered again typically by phosphate-buffered saline as described hereinabove to maintain a pH within the range of about 7.0 to 7.4. The most particularly preferred polymer is polyvinylpyrrolidone of an average molecular weight of about 10K.

The most preferred reconstitution buffer will be a solution comprising potassium chloride, sodium chloride and sodium phosphate and potassium dihydrogen phosphate, all of which form a basic salt buffer at a pH of about 7.2, which also contains about 19% weight by volume of polyvinylpyrrolidone (average molecular weight about 10K).

The reconstitution solution may also optionally contain a monosaccharide, preferably present in the concentration range of about 7.0 to 37.5% weight to volume. The preferred monosaccharides are xylose, glucose, ribose, mannose and fructose.

In the most preferred embodiment, the lyophilized platelets can be reconstituted by mixing with an equal volume of the reconstitution buffer at a temperature of about 37° C. and mixed until fully hydrated. By "equal" it is meant that the volume is the same as the starting volume prior to lyophilization. After reconstitution, the solution is preferably diluted 1:1 with dextrose-saline solution, at pH 7 and 290 mOsm.

Then, it is preferred that the rehydrated platelets be washed according to the following procedure. It is realized, however, that once the platelets are reconstituted with reconstitution buffer they are in a transfusably-useful form, but the combination of washings described hereinafter are preferred, specifically for clinical purposes.

After separating the platelets from the reconstitution buffer by centrifugation, the resulting packed platelets, usually in the form of a pellet, are preferably resuspended in (approximately the volume used in the reconstitution) a buffer comprising the basic salt buffer at pH 7.2, described above, further containing about 10% weight by volume polyvinylpyrrolidone (molecular weight about 2.5K). Separation by centrifugation completes the first post-rehydration step, a washing step. The platelets can be used as is or be returned to autologous plasma.

The reconstituted cells according to the present invention have characteristics which render them transfusable and useful for therapeutic purposes in that their properties are similar to that of normal (i.e. not previously lyophilized) platelets. Typically reconstituted platelets according to the present invention aggregate in the range of about 25–80% when stimulated with ADP. The recovery of platelets is usually at least 20% by number, and on an average of 50–80%, with normal discoid or spherical morphology. In some runs nearly 100% recovery may be obtainable. In addition, the recovered cells are capable of phagocytosis, which is an indication that normal citric acid cycle and mitochondrial function are preserved.

Having described the preferred embodiments of the present invention, the following examples are provided by way of illustration but are not intended to limit the invention in any way.

EXAMPLE I

Samples of platelets stored for 2-4 days as platelet concentrates in CPDA were prepared for lyophilization by mixing a proportion of the platelet concentrate with lyophilization buffer in a 1:5 ratio by volume at room temperature.

The lyophilization buffer was composed of the following:

| 20% PVP Lyobuffer | | |
|---|---|---|
| KCl | 2.0 mM | pH 7.2 ± 0.05 |
| KH$_2$PO$_4$ | 1.47 mM | 2700 ± 200 mOsm |
| NaCl | 91.9 mM | |
| Na$_2$HPO$_4$ | 8.1 mM | |
| Inosine | 10.0 mM | |
| Adenine | 5.0 mM | |
| Nicotinic Acid | 0.75 mM | |
| Glutamine | .75 mM | |
| MgCl$_2$.6H$_2$O | .49 mM | |
| Glucose | 1.9 M | |
| Plasdone 24K | 200.0 g/l | |

This mixture was placed in a round bottom flask which ws subsequently immersed in liquid N$_2$ (−196° C.) with swirling to evenly distribute sample on the walls of the flask. The flasks were then placed under vacuum on a Labconco Model 4.5 Bench Top Lyophilizer. Vacuum was maintained at 5-10 mTorr with a condenser temperature of −50 to −60° C. The sample was allowed to dry in this manner for 12-16 hours until the flask had returned to room temperature and contents were brittle to touch.

Samples were reconstituted by mixing a volume equal to the original volume of the following reconstitution bufffer with the dried material at 37° C.

| Reconstitution Buffer | | |
|---|---|---|
| KCl | 2.0 mM | pH 7.20 ± 0.05 |
| KH$_2$PO$_4$ | 1.47 mM | 605 ± 15 mOsm |
| NaCl | 110.7 mM | |
| Na$_2$HPO$_4$ | 8.1 mM | |
| Plasdone C-15 | 190.0 g/l | |

This solution was swirled until all dry material was rehydrated. Following this, a 1:1 volume of dextrose-saline, at pH 7.0 and 290-300 mOsm was mixed with the reconstituted platelet suspension. Samples were then scored for morphology and counted using a Serono-Baker system 9000 Automated Hematology Analyzer to determine percentage recovery. Values are recorded below:

TABLE 1

| Sample # | *Yield | **Morphology Score |
|---|---|---|
| 1 | 106% | — |
| 2 | 107% | 160 |

*Yield = $\left[ \dfrac{\text{\# of platelets after lyophilization}}{\text{\# of platelets before lyophilization}} \right] \times 100$

**Morphology Score
0: dead cells, balloons   a
1: pseudopodia   b
2: spheres   c
4: discs   d
Score = (0 * a + 1 * b + 2 * C + 4 * d)/2
Maximum = 400
Based on 200 cells counted.

EXAMPLE II

The procedure described in Example I was repeated using various lyophilization buffers.

TABLE 2

| Lyo Buffer Used 5% 24K PVP/15% M-HES Lyophilization Buffer | | Sample # | Score | Yield |
|---|---|---|---|---|
| KCl | 2.0 mM | 1 | 182 | 58 |
| KH$_2$PO$_4$ | 1.47 mM | 2 | 157 | 58 |
| NaCl | 91.9 mM | 3 | 163 | 75 |
| Na$_2$HPO$_4$ | 8.1 mM | Avg. | 167 ± 13 | 64 ± 9.8 |
| Inosine | 10.0 mM | | pH 7.20 ± 0.05 | |
| Adenine | 5.0 mM | | 3800 ± 200 mOsm | |
| Nicotinic Acid | .75 mM | | | |
| Glutamine | .75 mM | | | |
| MgCl$_2$.6H$_2$O | .49 mM | | | |
| Glucose | 2.3 M | | | |
| Plasdone 24K | 50.0 g/l | | | |
| M-HES | 150.0 g/l | | | |

EXAMPLE III

The procedure described in Example I was repeated using a different reconstitution buffer.

TABLE 3

| Reconstitution Buffer PVP-Dextrose Saline | | Sample # | Score | Yield |
|---|---|---|---|---|
| Glucose | 10.0 mM | 1 | 150 | 52.6% |
| Na$_2$HPO$_4$ | .71 g/l | | | |
| Plasdone 2.5K | 100.0 g/l | | | |
| NaCl | 68.4 mM | | | |
| pH 7.2 ± 0.05 | | | | |
| 283 ± 15 mOsm | | | | |

EXAMPLE IV

The procedure described in Example I was repeated except:
(1) Platelet-rich plasma from freshly drawn blood in 0.38% trisodium citrate was used.
(2) The reconstitution in Example III was used.
(3) The platelets were resuspended in autologous plasma.

Platelet aggregation was determined as follows:

The platelet concentration was adjusted to about 215×10$^6$ platelets/ml. 100 μl of 200 μM ADP was added to 900 μl of the sample with stirring in a cuvet. The sample was examined through use of a fluorimeter with excitation and emission set at 520 nm. In this manner, light scattering at a 90° angle can be used to detect turbidity changes. Shape change and aggregation are characterized by a decrease in light scatter.

The decrease in light scatter is reported as a percentage of the decrease seen when the same procedure is carried out with platelets stored for various times at room temperature.

TABLE 4

| Sample # | Score | Yield | Aggregation | |
|---|---|---|---|---|
| | | | vs. Fresh | vs. 24 hr old |
| 1 | 117 | 48.4% | 29.5% | 81.0% |

EXAMPLE 5

The procedure described in Example III was repeated.

The ability of reconstituted platelets to phagocytose beads was evaluated as follows:

Ten μl of 0.15 micron fluorescent latex beads (1.25% solids) (Polysciences, Inc.) was added to 50 μl reconstituted platelets at 37° C. The cells were incubated with the beads for 45 minutes at 37° C. They were then stained with 2 μl of 2 mg/ml rhodamine stain, $R_{18}$ (Molecular Probes, Inc.) at room temperature in the dark for 30 minutes or more. They were then examined under a fluorescent microscope and showed internalization of the beads.

From the foregoing description, one skilled in the art can readily ascertain that essential characteristics of the invention and, without departing from the spirit and scope thereof, can adapt the invention to various usages and conditions. Changes in form and substitution of equivalents are contemplated as circumstances may suggest or render expedient, and although specific terms have been employed herein, they are intended in a descriptive sense and not for purposes of limitation.

What is claimed is:

1. A lyophilized platelet-containing composition containing about 3% by weight or less of moisture prepared by lyophilization of an aqueous suspension of platelets in a phosphate buffered saline solution at a pH in the range of 7.0 to 7.4 comprising a final concentration of about 7 to 37.5% by weight of a monosaccharide or mixture of monosaccharides and a final concentration of about 0.7% by weight percent up to the saturation point of the solution of a polymer or mixture of polymers having a molecular weight in the range of about 1K to 600K.

2. A composition according to claim 1 wherein said polymers are amphipathic.

3. A composition according to claim 1 wherein said polymers have a molecular weight in the range of about 2.5K to 360K.

4. A composition according to claim 1 wherein said monosaccharide is selected from the group consisting of xylose, glucose, ribose, mannose and fructose.

5. A composition according to claim 4 wherein said monosaccharide comprises glucose.

6. A composition according to claim 3 wherein said polymer is selected from the group consisting of polyvinylpyrrolidone, hydroxyethyl starch, dextran and mixtures thereof.

7. A composition according to claim 6 wherein said polymer comprises polyvinylpyrrolidone.

8. A composition according to claim 7 wherein the final concentration of said polyvinylpyrrolidone in said solution is in the range of 12 to 20% by weight and has an average molecular weight of 10-40K.

9. A composition according to claim 7 wherein said polyvinylpyrrolidone has an average molecular weight of about 24K.

10. A composition according to claim 7 wherein said polyvinylpyrolidone has an average molecular weight of about 360K.

11. A composition according to claim 9 or 10 wherein said composition comprises a mixture of polyvinylpyrrolidone and hydroxyethyl starch.

12. A composition according to claim 11 wherein said hydroxyethyl starch has an average molecular weight of about 500K.

13. A process of reconstituting lyophilized platelets to a transfusably-useful state, wherein said lyophilized platelets consist essentially of a composition according to claim 1 comprising the step of:
   mixing said composition with a sufficient volume of a phosphate-buffered saline reconstitution solution having a pH in the range of about 7.0-7.4 at a temperature in the range of about 15-50° C., said reconstitution solution comprising a final concentration of about 0.7% by weight up to the saturation concentration of a polymer or mixture of polymers having a molecular weight in the range of about 1K to 360K, to form platelets in a transfusably-useful state.

14. A process according to claim 13 wherein said polymers are amphipathic.

15. A process according to claim 13 wherein said polymers have a molecular weight in the range of about 2.5K to 360K.

16. A process according to claim 13, 14 or 15 further comprising the steps of:
   separating said platelets from said reconstitution solution by centrifugation and washing said platelets by at least one wash cycle by resuspending said platelets in a dextrose-saline buffer solution at a pH in the range of about 7.0-7.4 and separating said platelets from said buffer solution by centrifugation.

17. A transfusably useful platelet-containing composition made according to the process of claim 13.

18. A transfusably useful platelet-containing composition made according to the process of claim 16.

19. A process of reconstituting a lyophilized composition comprising platelets comprising the step of contacting said platelets at a temperature greater than about 17° C. with an aqueous solution of a polymer or mixture of polymers having a molecular weight of from about 1K to about 600K which is present in a final concentration in the range of 10 to 30% by weight.

20. A process according to claim 19 wherein said polymers are amphipathic.

21. A process according to claim 19 where said polymers have a molecular weight in the range of about 2.5K to 360K.

22. A process according to claim 19, 20 or 21 wherein said polymer is selected from the group consisting of polyvinylpyrrolidone, hydroxyethyl starch, dextran and mixtures thereof.

23. A process according to claim 20 wherein said polymer comprises polyvinylpyrrolidone of average molecular weight of about 10K.

24. A process according to claim 19, 20 or 21 wherein said solution further comprises a monosaccharide in a final concentration of about 7.0 to 37.5% by weight.

25. A transfusably-useful platelet composition reconstituted from a dried state comprising
   platelets characterized by a reconstituted recovery of at least about 20% by weight, based on the number of the platelets prior to drying; which aggregate about 25-80% upon stimulation with ADP and are capable of phagocytosis;
   and further comprising a polymer or mixture of polymers having a molecular weight of from about 1K to about 600K in a concentration of about 10 to 30% by weight, wherein said polymer is selected from the group consisting of polyvinylpyrrolidone, hydroxyethyl starch, dextran and mixtures thereof.

26. A composition according to claim 25 wherein said polymer comprises polyvinylpyrrolidone of average molecular weight of about 10K.

27. A composition according to claim 25 wherein said solution further comprises a monosaccharide in a final concentration of about 7.0 to 37.5% by weight.

28. A process for the lyophilization of platelets comprising:

immersing a plurality of platelets in a buffered solution which includes:
a monosaccharide which is present in the solution in a concentration of from about 7.0 to 37.5%, and
a polymer, or a mixture of polymers, each of said polymers having a number average molecular weight in the range of about 1K to about 600K, wherein the total concentration of said polymers is of from about 0.7% up to saturation in the solution; freezing the solution; and drying the cells by sublimation of the water.

29. The process of claim 28 wherein said polymers are amphipathic.

30. The process of claim 28 wherein one of said polymers has a molecular weight in the range of about 2.5K to about 360K.

31. The process of claim 28 wherein the monosaccharide is selected from the group consisting of xylose, glucose, ribose, mannose and fructose.

32. The process of claim 28 wherein said mixture of polymers comprises polyvinylpyrrolidone and hydroxyethyl starch.

33. The process of claim 28 wherein said polymer comprises polyvinylpyrrolidone.

34. The process of claim 32 or 33 wherein said polyvinylpyrrolidone has an average molecular weight of about 24K.

35. The process of claim 32 or 33 wherein said polyvinylpyrrolidone has an average molecular weight of about 360K.

36. The process according to claim 32 wherein said hydroxyethyl starch has an average molecular weight of about 500K.

* * * * *

UNITED STATES PATENT AND TRADEMARK OFFICE
CERTIFICATE OF CORRECTION

PATENT NO. : 5,213,814
DATED : May 25, 1993
INVENTOR(S) : Raymond P. Goodrich, Jr., et al It is certified that error appears in the above-indentified patent and that said Letters Patent is hereby corrected as shown below:

Column 7, line 25 "ws" should be --was--.

Column 7, line 37 "bufffer" should be --buffer--.

Signed and Sealed this

Twenty-fifth Day of January, 1994

Attest:

BRUCE LEHMAN

*Attesting Officer*    *Commissioner of Patents and Trademarks*